US005345281A

United States Patent [19]

Taboada et al.

[11] Patent Number: 5,345,281
[45] Date of Patent: Sep. 6, 1994

[54] EYE TRACKING SYSTEM AND METHOD

[76] Inventors: John Taboada, 12530 Elm Country, San Antonio, Tex. 78230; William Robinson, 12324 Starcrest #105, San Antonio, Tex. 78216

[21] Appl. No.: 992,182

[22] Filed: Dec. 17, 1992

[51] Int. Cl.⁵ .............................................. A61B 3/14
[52] U.S. Cl. .................... 351/210; 351/209; 351/246
[58] Field of Search ............... 351/210, 209, 221, 220, 351/200, 201, 246

[56] References Cited

U.S. PATENT DOCUMENTS

| 4,145,122 | 3/1979 | Rinard et al. | 351/7 |
| 4,287,410 | 9/1981 | Crane et al. | 250/201 |
| 4,373,787 | 2/1983 | Crane et al. | 351/210 |
| 4,541,697 | 9/1985 | Remijam | 351/211 |
| 4,613,219 | 9/1986 | Vogel | 351/209 |
| 4,856,891 | 8/1989 | Pflibsen et al. | 351/210 |
| 4,889,422 | 12/1989 | Pavlidis | 351/210 |
| 4,950,069 | 8/1990 | Hutchinson | 351/210 |
| 5,231,674 | 7/1993 | Cleveland et al. | 351/210 |

*Primary Examiner*—William L. Sikes
*Assistant Examiner*—Hung Xuan Dang
*Attorney, Agent, or Firm*—Bobby D. Scearce; Thomas L. Kundert

[57] ABSTRACT

System and method for tracking the gaze of the human eye are described which comprise directing an infrared light beam along an optical axis into the eye, and displaying the reflected optical light distribution on a position sensing detector to determine eye position, considering the differences in infrared reflectivities between the pupil and the surrounding iris and sclera.

18 Claims, 3 Drawing Sheets

EYE TRACKING SYSTEM AND METHOD

RIGHTS OF THE GOVERNMENT

The invention described herein may be manufactured and used by or for the Government of the United States for all governmental purposes without the payment of any royalty.

BACKGROUND OF THE INVENTION

The present invention relates generally to devices for tracking the gaze of the human eye, and more particularly to an optical device for tracking eye movement by analysis of the reflection off the eye of an infrared (IR) beam.

Existing systems for tracking eye movement include electronystagmography methods and magnetic tracking of scleral induction coils imbedded in annuli attached to the eye with a contact lens. These methods are invasive and of limited accuracy and generally require careful subject preparation, substantially constant recorder calibration and a controlled laboratory environment. Another system uses differences in IR light reflected from the iris and sclera as detected by a pair of photodetectors, which differences are linearly related to eye rotation over a range of about ±25°. This system can accurately track the limbus horizontally but not vertically, since the limbus is partially occluded by the eyelid, and requires apparatus the placement of which partially obstructs the vision of the subject.

It is a principal object of the invention to provide a method and apparatus for real time, non-invasive and nonoccluding measurement of eye position.

It is a further object of the invention to provide two dimensional tracking of the human eye, including indication of horizontal and vertical position of the eye.

It is a further object of the invention to provide compact, lightweight and portable apparatus for eye tracking.

It is another object of the invention to provide means for fixation monitoring in field-of-vision testing.

It is yet another object of the invention to provide means for tracking both eyes in stereoscopic vision in tracking the fixation point of a subject's gaze in a three-dimensional volume of space.

It is yet another object of the invention to provide means for computer cursor positioning using eye movement.

It is yet another object of the invention to provide means for two-dimensional eye gaze control of a cursor in a computer display.

It is yet another object of the invention to provide means for three-dimensional control of a cursor in a stereoscopic computer display.

These and other objects of the invention will become apparent as a detailed description of representative embodiments proceeds.

SUMMARY OF THE INVENTION

In accordance with the foregoing principles and objects of the invention, system and method for tracking the gaze of the eye are described which comprise directing an infrared light beam along an optical axis into the eye, and displaying the reflected optical light distribution on a position sensing detector to determine eye position, considering the differences in infrared reflectivities between the pupil and the surrounding iris and sclera.

DESCRIPTION OF THE DRAWINGS

The invention will be more clearly understood from the following detailed description of representative embodiments thereof read in conjunction with the accompanying drawings wherein.

DETAILED DESCRIPTION

Figure 1:
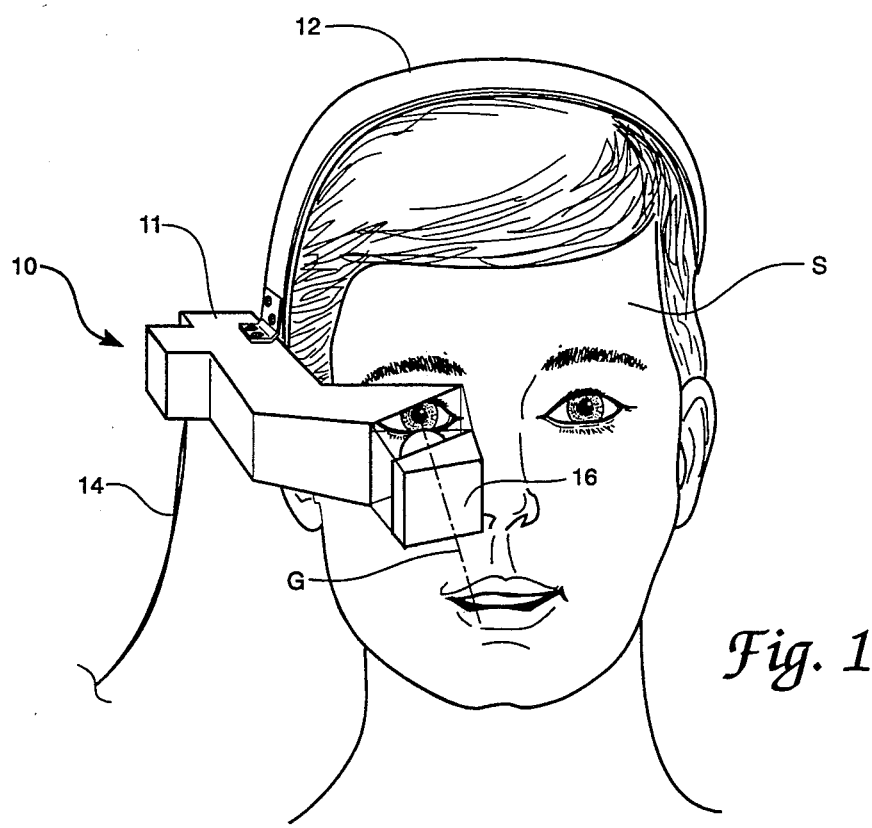
FIG. 1 is a perspective view of one embodiment of the invention as applied to a subject.

Referring to FIG. 1, shown therein is a perspective view of an embodiment of the invention as applied to subject S. Device 10 of FIG. 1 may comprise generally a suitable housing 11 enclosing the various optical, light source and electronic detection elements described in detail below in relation to FIGS. 2–6. Headband 12 supports device 10 on subject S. Cable 14 provides means for supplying power to the light sources contained within device 10 and for conducting signals therefrom in the practice of the invention. Controllable presentation 16 may be attached to housing 11 as suggested in FIG. 1 or provided as a separate display (not shown) for presenting images for observation by subject S along viewing axis G in the controlled tracking of eye movement as discussed fully below. It should be noted at the outset that the embodiments of the invention described herein as illustrative are directed to configurations applied to only one eye, but it is understood that embodiments including devices applied to either eye or to both eyes simultaneously are included within the scope of these teachings and of the appended claims. It is emphasized that in applying a system to each eye, tracking of the gaze in real or virtual three-dimensional space may be accomplished.

Figure 2:
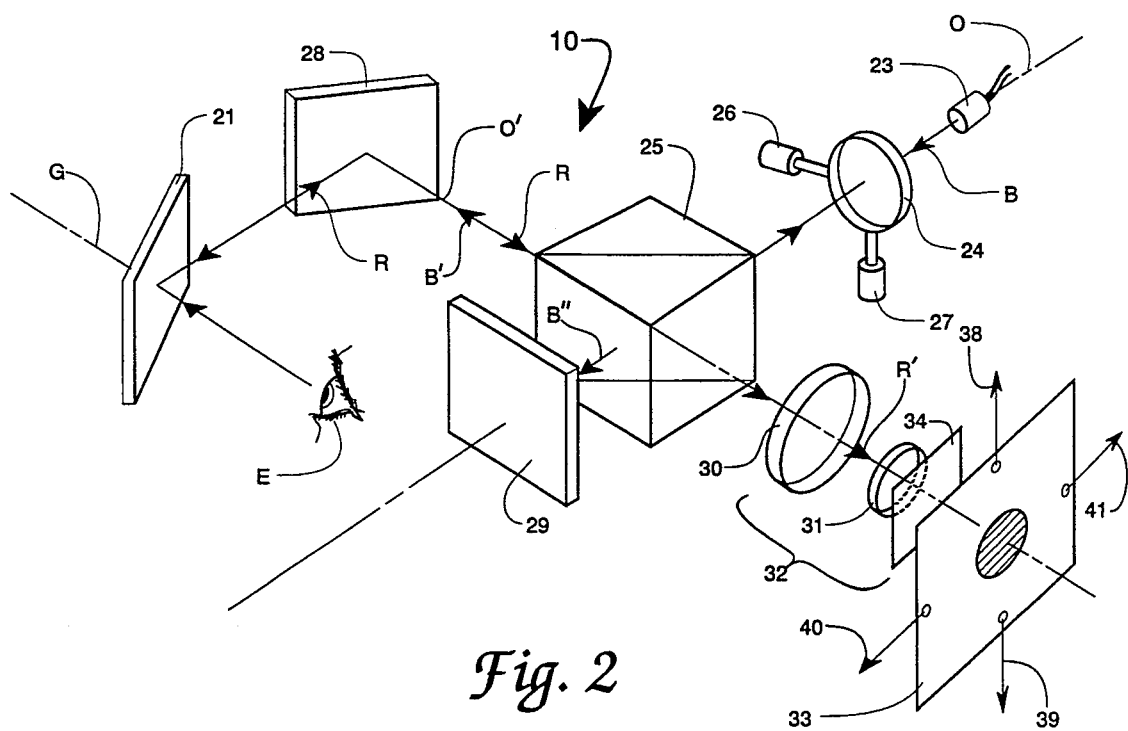
FIG. 2 is a schematic view of the optical elements comprising the FIG. 1 device.

Referring now to FIG. 2, shown therein is a drawing of elements comprising the internal structure of eye tracking device 10. Dichroic beamsplitter 21 is disposed along viewing axis G to reflect into eye E substantially all near infrared (IR) radiation above about 700 nm (e.g., 850 nm) while transmitting along axis G substantially all visible light (about 400 to 700 nm) as not to substantially interfere with the view of eye E. Source 23 of IR radiation is positioned to transmit IR beam B along optical axis O through collimating lens 24 and beamsplitter 25. Source 23 is any suitable IR source as would occur to the skilled artisan, such as a GaAs light emitting diode, laser source, or other light source filtered to pass only near IR (700–1100 nm). Motorized positioners 26,27 may be operatively connected to lens 24 in order to track the pupil. Beamsplitter 25 is a polarizing type disposed to reflect vertically polarized (polarization selection is not critical) portion B' of beam B along axis O' and to transmit horizontally polarized portion B'' to an absorbing target 29. Mirror 28 may be suitably disposed along axis O' for folding beam B' toward beamsplitter 21 and into eye E. The IR illumination of eye E by beam B' is highly reflected by the iris and sclera, but only slightly reflected by the pupil. Portion R of beam B' reflected by eye E is projected back along axis O' toward beamsplitter 25. Vertically polarized radiation in reflected beam portion R is reflected by beamsplitter 25 toward source 23, but depolarized, scattered radiation is transmitted along axis O' as IR image R' of eye E. Objective lens 30 and eyepiece 31 comprising telescope system 32 are disposed along axis O' substantially as shown for projecting image R' onto position sensing detector 33. Dichroic filter 34 may be disposed in front of detector 33 to filter out all but the IR radiation in image R'.

The pupil image appears on detector 33 as a bright generally circular spot surrounded by a dark region defining the image of the iris, and eye position can be determined from data derivable from the pupil image. This requires a two-dimensional position sensitive detector 33. Detector 33 may be any type suitable for the purpose, such as a United Detector Technology PIN-Sc position sensitive detector which provides stable output, fast response time and about 0.0001 inch resolution. Output signals 38–41 define detector 33 response and the corresponding pupil image position relative to axis O'.

Figure 3:
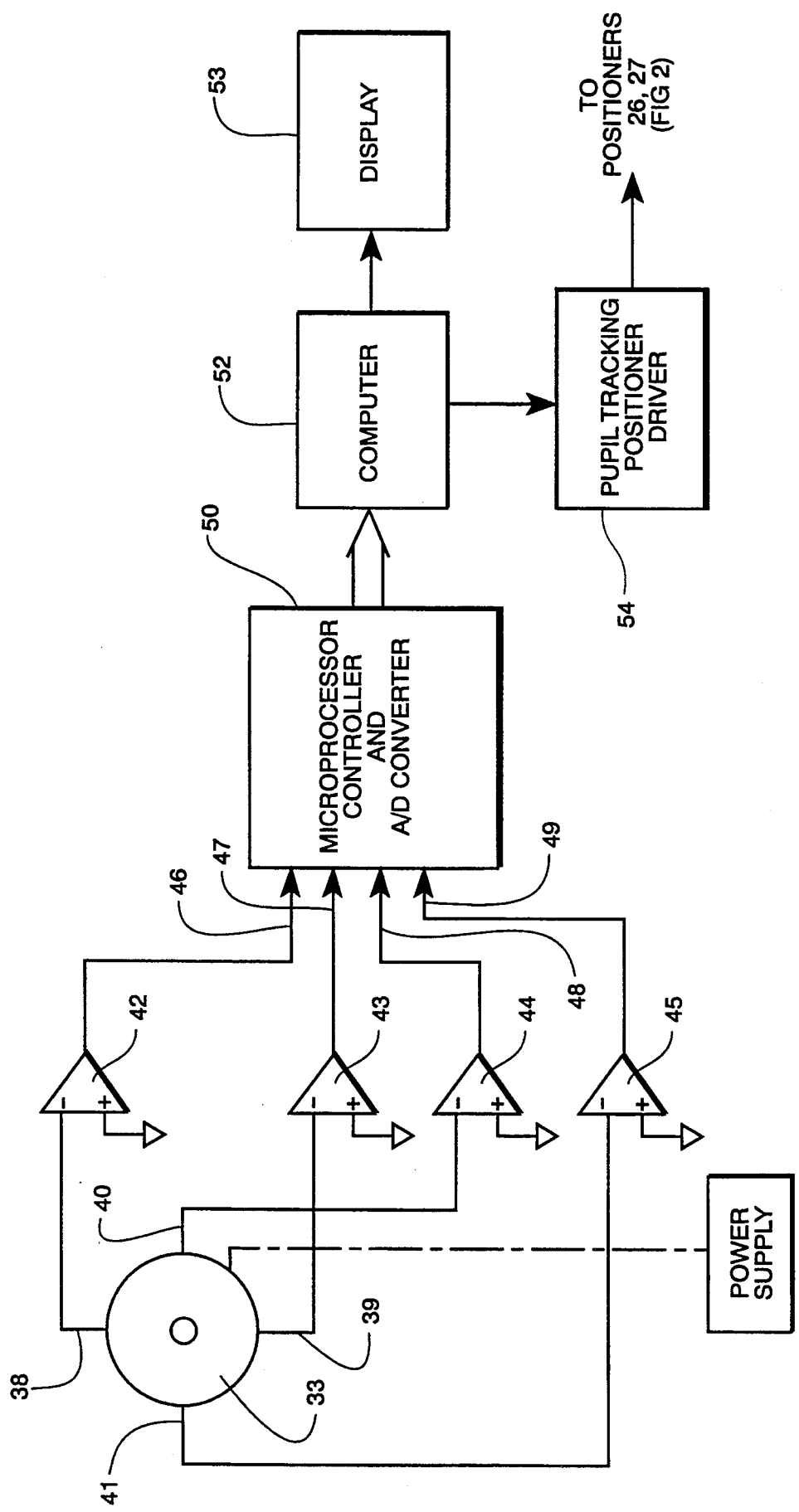
FIG. 3 is a schematic of the essential electronic components for generating x,y coordinates of eye position using the device of FIGS. 1 and 2.

Referring now to FIG. 3, shown therein is a schematic of the essential electronic components for analyzing signals 38–41 defining x,y position coordinates of the pupil image on detector 33. Signals 38–41 are input to respective variable gain transimpedance amplifiers 42–45 which convert detector 33 currents into analog voltages. Voltage output signals 46–49 from amplifiers 42–45 are input to microprocessor controller and analog to digital converter 50 (e.g., Motorola 6811 microprocessor) which sequentially samples the inputs at Nyquist or higher rates. The vertical (y) and horizontal (x) positions of eye E are derived by determining the position of the light pupil image position according to the following relationships:

$$y = \frac{\text{Signal 46} - \text{Signal 47}}{|\text{Signal 46}| + |\text{Signal 47}|}$$

$$x = \frac{\text{Signal 48} - \text{Signal 49}}{|\text{Signal 48}| + |\text{Signal 49}|}$$

Although the numerators (signal differences) in each equation would suffice for defining eye position, each signal difference is divided by the corresponding sum to cancel fluctuations in intensity level which might affect signal difference and present a false eye position. The x,y coordinates may be calculated by microprocessor 50 and sent to computer 52 via suitable a suitable interface. Memory resident software interprets the data sent and displays a cursor position on corresponding display 53. Computer 52 may also send tracking signals to pupil tracking positioner driver 54.

Figure 4:
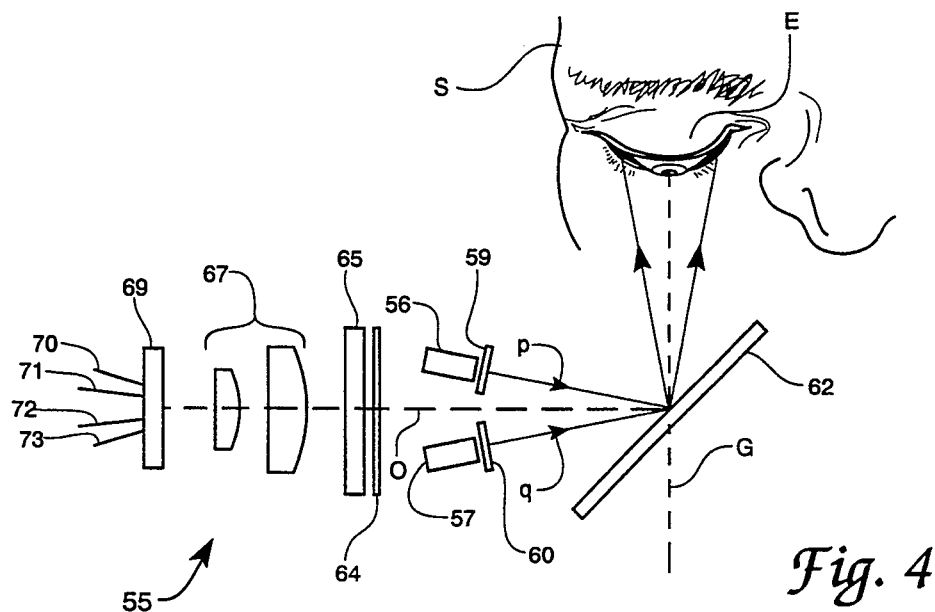
FIG. 4 is a schematic of the arrangement of optical elements in a device for tracking the pupil as a dark field.

Referring now to FIG. 4, shown therein is a schematic of another optical system 55 according to the invention for tracking the pupil. A pair of IR light emitting diodes 56,57 are disposed for directing respective IR beams p,q into eye E. Beams p,q are identically polarized (e.g. vertically) by suitably placed polarizing filters 59,60. Beams p,q are reflected into eye E using dichroic mirror 62 which reflects about 99% IR but passes about 90% visible light. That portion of beams p,q reflected by the iris and sclera back along viewing axis G is reflected along axis O through filter 64 for filtering (horizontal) polarization and through filter 66 for passing only IR and for removing unwanted reflections from the corneal surface and other stray light. Fast imaging lens system 67 focuses the (dark) image of the pupil onto two-axis position sensing detector 69. Position signals 70–73 from detector 69 are processed substantially as described above for signals 38–41 of system 10 of FIGS. 2 and 3. It may be noted that the system of FIG. 4 as well as that of FIG. 2 are insensitive to pupil diameter fluctuations and are compact, lightweight and easily head-mounted.

Figure 5:
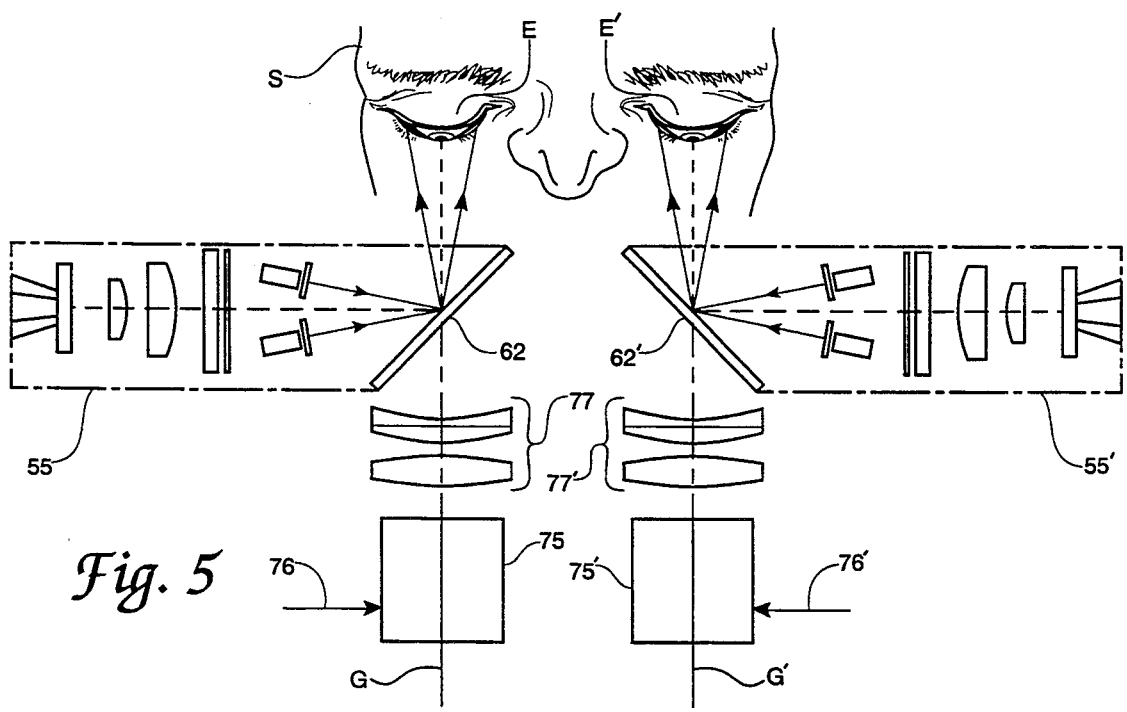
FIG. 5 is a schematic of the arrangement of optical elements for simultaneous tracking of the pupil as a dark field and for presentation of a computer monitor display.

Referring now to FIG. 5, shown therein is a schematic of a combination of optical elements for tracking the pupil according to FIG. 4 and for presenting a computer monitor display. Accordingly, system 55 may be mounted for viewing by subject S as in FIG. 4, and, additionally, (miniature) CRT display 75 or other suitable display may be helmet mounted or otherwise supported along axis G for use in conjunction with system 55. Display 75 may be configured to receive signal 76 characteristic of eye position from the computer (e.g., FIG. 3 #52). Subject S may then, with the aid of conjugate focusing lens system 77 view a cursor on display 75. Cursor position may be designated as (or related to) the actual gaze angle coordinate of eye E, so that subject S may position the curser on display 75 simply by moving eye E to the desired location on display 75. As suggested above, an additional system 55' and display 75' may be presented to the other eye of subject S so that each eye tracks the cursor on the corresponding display. With such an arrangement applied to each eye, the cursor assumes three dimensional virtual reality. The computer controlling signals to displays 75 may be configured to compensate for stereopsis by appropriate linear transformations of cursor data for each eye, and subject S may position the cursor in virtual three dimensional space.

The invention therefore provides system and method for tracking eye position. It is understood that modifications to the invention may be made as might occur to one with skill in the field of the invention within the scope of the appended claims. All embodiments contemplated hereunder which achieve the objects of the invention have therefore not been shown in complete detail. Other embodiments may be developed without departing from the spirit of the invention or from the scope of the appended claims.

We claim:

1. A system for measuring the angular gaze position of the human eye, comprising:
   (a) a source of infrared light;
   (b) first optical means for directing a light beam from said source along a first optical axis into an eye of a subject;
   (c) dichroic beamsplitter means disposed along said first optical axis for simultaneously directing said light beam into said eye and transmitting into said eye visual images along a viewing axis of said eye;
   (d) second optical means for directing a reflected beam from said eye along a second optical axis and for forming an image of the pupil and surrounding iris and sclera of said eye, said image comprising a bright spot defining said pupil surrounded by a dark region defining said iris and sclera; and
   (e) two-dimensional light position sensing means disposed along said second optical axis for detecting the position of said dark spot relative to said second optical axis and for providing a signal corresponding to the position of said pupil relative to said first optical axis.

2. The system of claim 1 further comprising directing means controllable by said signal from said two-dimensional light position sensing means for controllably directing said light beam into said eye.

3. The system of claim 2 wherein said directing means includes a microprocessor controller with analog-to-digital converter and microcomputer for providing signals for controllably directing said light beam into said eye.

4. The system of claim 3 further comprising means for displaying the position of said pupil.

5. The system of claim 1 wherein said source of infrared light is selected from the group consisting of a gallium arsenide light emitting diode and a laser source.

6. The system of claim 1 wherein said dichroic beamsplitter means is a polarizing type disposed to reflect one of the vertically and horizontally polarized light of said light beam from said source and to transmit the other of said vertically and horizontally polarized light of said light beam.

7. The system of claim 1 wherein said two-dimensional position sensing means comprises a two-axis position sensitive photo detector.

8. A system for tracking the gaze of the human eye, comprising:
(a) a source of infrared light;
(b) first optical means for directing a light beam from said source along a first optical axis into an eye of a subject, said first optical means including dichroic beamsplitter means disposed along said first optical axis and alignable with the pupil of said eye and along a viewing axis of said eye for simultaneously directing said light beam into said eye and transmitting into said eye visual images along said viewing axis;
(c) second optical means for directing a reflected beam from said eye along a second optical axis and for forming an image of the pupil and surrounding iris and sclera of said eye, said image comprising a dark spot defining said pupil surrounded by a bright region defining said iris and sclera; and
(d) two-dimensional position sensing means disposed along said second optical axis for detecting the position of said dark spot relative to said second optical axis and for providing a signal corresponding to the position of said pupil relative to said first optical axis.

9. The system of claim 8 wherein said source of infrared light is selected from the group consisting of a gallium arsenide light emitting diode and a laser source.

10. The system of claim 8 wherein said dichroic beamsplitter means is a polarizing type disposed to reflect one of the vertically and horizontally polarized light of said light beam from said source and to transmit the other of said vertically and horizontally polarized light of said light beam.

11. The system of claim 8 wherein said infrared light is polarized, and further comprising filter means for filtering from said reflected beam light corresponding to reflections from said iris and sclera.

12. The system of claim 8 wherein said two-dimensional position sensing means comprises a two-axis position sensitive photo detector.

13. The system of claim 8 further comprising directing means controllable by said signal from said two-dimensional light position sensing means for controllably directing said light beam into said eye, said directing means including a microprocessor controller with analog-to-digital converter and microcomputer for providing signals for controllably directing said light beam into said eye.

14. A system for two-dimensional control of cursor position on a computer video display using eye movement, comprising:
(a) a source of infrared light;
(b) first optical means for directing a light beam from said source along a first optical axis into an eye of a subject, said first optical means including dichroic beamsplitter means disposed along said first optical axis and alignable with the pupil of said eye along a viewing axis of said eye for simultaneously directing said light beam into said eye and transmitting into said eye visual images along said viewing axis;
(c) second optical means for directing a reflected beam from said eye along a second optical axis and for forming an image of the pupil and surrounding iris and sclera of said eye, said image comprising a dark spot defining said pupil surrounded by a bright region defining said iris and sclera;
(d) two-dimensional position sensing means disposed along said second optical axis for detecting the position of said dark spot relative to said second optical axis and for providing a signal corresponding to the position of said pupil relative to said first optical axis; and
(e) electronic means for receiving said signal and for displaying said signal as a cursor position on a computer video display corresponding to the position of said pupil relative to said viewing axis of said eye.

15. The system of claim 14 wherein said dichroic beamsplitter means is a polarizing type disposed to reflect one of the vertically and horizontally polarized light of said light beam from said source and to transmit the other of said vertically and horizontally polarized light of said light beam.

16. A system for two-dimensional control of cursor position on a computer video display using eye movement, comprising:
(a) a source of infrared light comprising first and second infrared light emitting diodes;
(b) first optical means for directing first and second light beams from corresponding said first and second light emitting diodes into an eye of a subject, said first optical means including polarizing filter means for identically polarizing said first and second light beams and including dichroic beamsplitter means alignable with the pupil of said eye along a viewing axis of said eye for simultaneously directing said first and second light beams into said eye and transmitting into said eye visual images along said viewing axis;
(c) second optical means for directing a reflected beam from said eye along an optical axis and for forming an image of the pupil and surrounding iris and sclera of said eye, said image comprising a dark spot defining said pupil surrounded by a bright region defining said iris and sclera;
(d) two-dimensional position sensing means disposed along said optical axis for detecting the position of said dark spot relative to said second optical axis and for providing a signal corresponding to the position of said pupil relative to said viewing axis; and (e) electronic means for receiving said signal and for displaying said signal as a cursor position on a computer video display corresponding to the position of said pupil relative to said viewing axis of said eye.

17. A method for tracking the gaze of the human eye, comprising the steps of:

(a) providing a source of infrared light;

(b) directing a light beam from said source along a first optical axis into an eye of a subject, utilizing first optical means including dichroic beamsplitter means disposed along said first optical axis and alignable with the pupil of said eye and along a viewing axis of said eye for simultaneously directing said light beam into said eye and, transmitting into said eye visual images along said viewing axis;

(c) directing a reflected beam from said eye along a second optical axis utilizing second optical means for forming an image of the pupil and surrounding iris and sclera of said eye, said image comprising a dark spot defining said pupil surrounded by a bright region defining said iris and sclera; and (d) detecting the position of said dark spot relative to said second optical axis corresponding to the position of said pupil relative to said first optical axis.

18. The method of claim 17 wherein said dichroic beamsplitter means is a polarizing type disposed to reflect one of the vertically and horizontally polarized light of said light beam from said source and to transmit the other of said vertically and horizontally polarized light of said light beam.

* * * * *